United States Patent
Klankermayer et al.

(10) Patent No.: US 10,434,504 B2
(45) Date of Patent: Oct. 8, 2019

(54) METHOD FOR REDUCTION OF ORGANIC MOLECULES

(71) Applicant: RHEINISCH-WESTFÄLISCHE TECHNISCHE HOCHSCHULE (RWTH) AACHEN, Aachen (DE)

(72) Inventors: Jürgen Klankermayer, Essen (DE); Walter Leitner, Aachen (DE); Markus Meuresch, Aachen (DE)

(73) Assignee: RHEINISCH-WESTFÄLISCHE TECHNISCHE HOCHSCHULE (RWTH) AACHEN, Aachen (DE)

( * ) Notice: Subject to any disclaimer, the term of this patent is extended or adjusted under 35 U.S.C. 154(b) by 0 days.

(21) Appl. No.: 16/201,519

(22) Filed: Nov. 27, 2018

(65) Prior Publication Data

US 2019/0134618 A1    May 9, 2019

Related U.S. Application Data

(63) Continuation of application No. 15/549,908, filed as application No. PCT/EP2015/052881 on Feb. 11, 2015, now Pat. No. 10,166,534.

(51) Int. Cl.
| | |
|---|---|
| *C07D 307/02* | (2006.01) |
| *B01J 31/24* | (2006.01) |
| *C07C 67/303* | (2006.01) |
| *C07D 307/06* | (2006.01) |
| *C07D 307/33* | (2006.01) |
| *C07C 29/17* | (2006.01) |

(52) U.S. Cl.
CPC ......... *B01J 31/2409* (2013.01); *C07C 29/177* (2013.01); *C07C 67/303* (2013.01); *C07D 307/06* (2013.01); *C07D 307/33* (2013.01); *B01J 2231/645* (2013.01); *B01J 2531/821* (2013.01)

(58) Field of Classification Search
CPC .. C07D 307/02; C07D 307/06; C07D 307/33; C07C 67/303; C07C 29/17; B01J 31/24; B01J 2231/641; B01J 2531/821
USPC .......................................................... 549/508
See application file for complete search history.

(56) References Cited

U.S. PATENT DOCUMENTS 10,166,534 B2 *  1/2019  Klankermayer ...... C07C 29/177

FOREIGN PATENT DOCUMENTS

| EP | 2 141 142 | 1/2010 |
|---|---|---|
| EP | 2653457 | 10/2013 |
| JP | 2006-206570 | 10/2006 |

OTHER PUBLICATIONS

Barbaro et al, "Synthesis and Characterization of Ruthenium (II) Complexes Containing Chiral Bis(ferrocenyl)—$P_3$ or -$P_2S$ Ligands. Asymmetric Transfer Hydrogenation of Acetophenone", *Organometallics*, Jun. 24, 1997, vol. 16, pp. 3004-3014.

Sues et al. "Flexible Syntheses of Tripodal Phosphine Ligans 1, 1, 2-Tris(diarylphosphino)ethane and Their Ruthenium $n^5$-$C_5Me_5$ Complexes", Organometallics, Sep. 24, 2012, vol. 31, No. 18, pp. 6589-6594.

International Search Report from corresponding International Application No. PCT/EP2015/052881 filed Feb. 11, 2015.

* cited by examiner

*Primary Examiner* — Taylor V Oh
(74) *Attorney, Agent, or Firm* — Davidson, Davidson & Kappel, LLC

(57) ABSTRACT

A method for the reduction organic molecules comprising a Ruthenium-Triphosphine complex with aromatic ligands at the phosphors which are ortho or meta substituted.

18 Claims, No Drawings

METHOD FOR REDUCTION OF ORGANIC MOLECULES

This application is a continuation of U.S. patent application Ser. No. 15/549,908, filed Aug. 9, 2017, which is a U.S. national phase application under 35 U.S.C. of § 371 of International Application No. PCT/EP2015/052881, filed Feb. 11, 2015, the disclosures of which are hereby incorporated by reference herein.

The present invention relates to a method for reducing organic molecules, especially by using Ruthenium-Triphosphine-complexes.

In the prior art, e.g. EP 2 653 457 and related applications, methods of reducing organic molecules by hydrogenation using Ruthenium-Phosphine complexes have been disclosed. Although these methods have proven themselves to be useful, there is a constant need for further improvement and therefore it is an object to provide alternative and/or improved Ruthenium-Phosphine complexes for the reduction of organic molecules This object is achieved in the present invention by a method for the reduction of organic molecules, comprising the step of:
a) hydrogenating at least one organic molecule in the presence of a Ruthenium-Triphosphine-complex whereby the triphosphine-complex comprises at least one aryl and/or heteroaryl moeity bound to a phosphine which is substituted in ortho and/or meta position to the phosphine.

The term "hydrogenation" in the sense of the present invention especially means and/or includes the reaction of an organic molecule with molecular hydrogen and/or a source of molecular hydrogen.

The term "organic molecule" in the sense of the present invention especially includes or means at least one molecule having a moiety which is susceptible for reduction via hydrogenation. Suitable moieties may include double or triple bonds (either carbon-carbon or carbon-oxygen or carbon-nitrogen) or bonds of carbon with a heteroatom like oxygen, nitrogen or sulfur.

Especially interesting organic molecules in this context are carboxylic acids or carbonic acid and their derivatives, including explicitly carbonic acid derivatives in aqueous environment that would not be considered "organic" in the strict sense. In particular, carboxylic acid derivatives include, but are not limited to, the free acids and their salts, esters, lactones, acyclic or cyclic anhydrides, amides, lactames, or imides. Carbonic acid derivatives include $CO_2$ itself, carbonic acid or its salts (bicarbonates or carbonates), acyclic or cyclic organic carbonates, carbamic acids and their salts, carbamates, urethanes, or ureas.

The term "phosphine" in the sense of the present invention especially means and/or includes trivalent phosphororganic compounds, especially compounds with the general formula $PR^1R^2R^3$, $R^1$ to $R^3$ being independent from each other an organic residue such as e.g. a substituted or unsubstituted alkyl, aryl and/or heteroaryl.

The term "Ruthenium-Triphosphine-complex" especially means and/or includes a ruthenium complex where in the coordination sphere of the ruthenium a trivalent phosphororganic component is present so that a bond (may it be a covalent and/or a coordination bond) between the ruthenium and the trivalent phosphororganic component is formed at least temporarily during the reaction.

The term "Triphosphine-complex" especially means and/or includes a complex comprising at least organic compound in which three trivalent phosphors are present.

It should be noted that not necessarily all of the phosphines are bound to the Ruthenium during step a). More especially not all of the phosphors may catalytically be involved in the reaction.

The term "at least one aryl moeity bound to a phosphine which is substituted in ortho or meta position to the phosphine" especially means and/or includes that the following moiety is present in the triphosphine-complex:

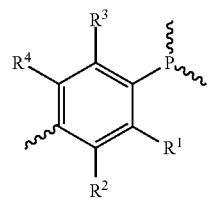

where at least one of $R^1$ to $R^4$ is not hydrogen (but the other may be) but an organic substituent, preferably selected out of the group comprising alkyl, aryl, heteroaryl, cycloalkyl, alkyloxy, aryloxy, alkenyl, perfluoroalkyl, Silyl, $SO_3$, amine and fluorene.

The term "at least one heteroaryl moeity bound to a phosphine which is substituted in ortho or meta position to the phosphine" has the same meaning mutatis mutandis with the same preferred organic substituents.

Surprisingly it has been found that by doing so the efficacy of the catalyst and/or the tolerance of the hydrogenation can be increased for most applications within the present invention, at least one of the following advantages could be observed:

The reaction can be performed at lower catalyst concentration

The reaction can for some catalysts even be carried out in the presence of water The reaction can be performed in the presence of solid acidic additives.

The reaction can be carried out at lower temperatures and pressures

The reaction can be performed under continuous-flow conditions

Without being bound to any theory the inventors believe that the ortho or meta substitution at the aromatic system bound to at least one of the phosphors in the complex leads to steric hindrance and thus at least partially prevents dimer or heteromer formation of the catalytic active species in the hydrogenation reaction. This is consistent with the very surprising discovery that when some Ruthenium-Triphosphine-complexes according to the present invention are used in hydrogenation reactions the reaction speed increases with decreasing (and not increasing) catalyst concentration in certain concentration areas.

It should be noted that the inventive Ruthenium-Triphosphine-complex may be used as a homogenous catalyst or in immobilized form. Also two-phase systems and phase-transfer-catalysis may be used depending on the actual application of the invention. Besides a reaction in batch mode, also a continuous reaction system is possible.

It should furthermore be noted that the Ruthenium-Triphosphine-complex may include other ligands such as (but not limited to) carbene, nitrogen containing-ligands such as amines or amides, phosphites, phosphoamidites, phosphoric ethers or esters etc.

Generic group definition: Throughout the description and claims generic groups have been used, for example alkyl, alkoxy, aryl. Unless otherwise specified the following are preferred groups that may be applied to generic groups found within compounds disclosed herein:
   alkyl: linear and branched C1-C8-alkyl,
   alkenyl: C2-C6-alkenyl,
   cycloalkyl: C3-C8-cycloalkyl,
   alkoxy: C1-C6-alkoxy,
   alkylene: selected from the group consisting of: methylene; 1,1-ethylene; 1,2-ethylene; 1,1-propylidene; 1,2-propylene; 1,3-propylene; 2,2-propylidene; butan-2-ol-1,4-diyl; propan-2-ol-1,3-diyl; 1,4-butylene; cyclohexane-1,1-diyl; cyclohexan-1,2-diyl; cyclohexan-1,3-diyl; cyclohexan-1,4-diyl; cyclopentane-1,1-diyl; cyclopentan-1,2-diyl; and cyclopentan-1,3-diyl,
   aryl: selected from homoaromatic compounds having a molecular weight under 300,
   arylene: selected from the group consisting of: 1,2-phenylene; 1,3-phenylene; 1,4-phenylene; 1,2-naphtalenylene; 1,3-naphtalenylene; 1,4-naphtalenylene; 2,3-naphtalenylene; 1-hydroxy-2,3-phenylene; 1-hydroxy-2,4-phenylene; 1-hydroxy-2,5-phenylene; and 1-hydroxy-2,6-phenylene,
   heteroaryl: selected from the group consisting of: furyl, pyridinyl; pyrimidinyl; pyrazinyl; triazolyl; pyridazinyl; 1,3,5-triazinyl; quinolinyl; isoquinolinyl; quinoxalinyl; imidazolyl; pyrazolyl; benzimidazolyl; thiazolyl; oxazolidinyl; pyrrolyl; carbazolyl; indolyl; and isoindolyl, wherein the heteroaryl may be connected to the compound via any atom in the ring of the selected heteroaryl, Unless otherwise specified the following are more preferred group restrictions that may be applied to groups found within compounds disclosed herein:
   alkyl: linear and branched C1-C6-alkyl, more preferred methyl, ethyl, propyl, butyl, t-butyl, sec-butyl, most preferred methyl, sec-butyl and t-butyl.
   alkenyl: C3-C6-alkenyl,
   cycloalkyl: C6-C8-cycloalkyl,
   alkoxy: C1-C4-alkoxy,
   alkylene: selected from the group consisting of: methylene; 1,2-ethylene; 1,3-propylene; butan-2-ol-1,4-diyl; 1,4-butylene; cyclohexane-1,1-diyl; cyclohexan-1,2-diyl; cyclohexan-1,4-diyl; cyclopentane-1,1-diyl; and cyclopentan-1,2-diyl,
   aryl: selected from group consisting of: phenyl; biphenyl; naphthalenyl; anthracenyl; and phenanthrenyl,
   arylene: selected from the group consisting of: 1,2-phenylene; 1,3-phenylene; 1,4-phenylene; 1,2-naphtalenylene; 1,4-naphtalenylene; 2,3-naphtalenylene and 1-hydroxy-2,6-phenylene,
   heteroaryl: selected from the group consisting of: furyl, pyridinyl; pyrrolyl and imidazolyl, wherein the heteroaryl may be connected to the compound via any atom in the ring of the selected heteroaryl,
   heteroarylene: selected from the group consisting of: pyridin 2,3-diyl; pyridin-2,4-diyl; pyridin-2,6-diyl; pyridin-3,5-diyl; quinolin-2,3-diyl; quinolin-2,4-diyl; isoquinolin-1,3-diyl; isoquinolin-1,4-diyl; pyrazol-3,5-diyl; and imidazole-2,4-diyl.

According to a preferred embodiment of the present invention, the Ruthenium-Triphosphine-complex comprises more than one Phosphine, i.e. that in the coordination sphere of the ruthenium two or more trivalent phosphororganic components are present so that bonds (may it be covalent or coordination bonds) between the ruthenium and the phosphororganic components are formed at least temporarily during the reaction. Especially preferred are Ruthenium-Triphosphine-Complexes.

It should be noted that the present invention is not limited to Ruthenium-Triphosphine-complexes where all phosphines are bound to the Ruthenium. Actually in many applications of the present invention, the phosphine is used in excess so that also non-bound phosphines are present.

Especially preferred for the present invention are Ruthenium-Triphosphine-complexes comprising phosphororganic compounds where the "bridging" moiety between the phosphors is an alkyl or alkylene moiety whereas the further ligands at the phosphor are aryl or heteroaryl, whereby one of these ligands is substituted in ortho and/or meta position According to a preferred embodiment of the present invention the Ruthenium-Triphosphine-complex comprises a phosphororganic compound where two or all three phosphors have a aryl and/or heteroaryl moeity which is substituted in ortho and/or meta position to the phosphine bound thereto. This has shown to greatly increase the reaction efficiency.

According to a preferred embodiment of the present invention the Ruthenium-Triphosphine-complex comprises a phosphororganic compound of the following structure

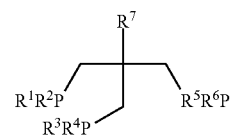

whereby $R^1$ to $R^6$ are independent from each other substituted or unsubstituted aryl or heteroaryl (provided that one of $R^1$ and $R^2$, $R^3$ and $R^4$, $R^5$ and $R^6$ is substituted in ortho and/or meta position to the phosphine) and $R^7$ is hydrogen or an organic moeity, preferably alkyl, cycloalkyl or aryl. Especially preferred $R^7$ is alkyl, more preferred methyl or ethyl.

It should be noticed that according to one preferred embodiment of the present invention, the Ruthenium-Triphosphine-complex may (prior to the reaction) comprise one or more "volatile" or easy removable ligand which stabilizes the complex so that it may be handled before the reaction but during the reaction sequence is replaced by the reactants. Suitable ligands are i.e. trimethylmethane, cyclopentadienyl, allyl, methylallyl, ethylene, cyclooctadiene, acetylactonate, acetate or carbon monoxide.

According to a preferred embodiment of the present invention, step a) is performed under acidic conditions. This has been shown to greatly increase the efficiency for most applications within the present invention.

The term "acidic conditions" in the sense of the present invention especially means and/or includes that during the reaction at least temporarily more acid than base is present.

According to a preferred embodiment of the present invention, step a) is performed under acidic conditions whereby the (initial) concentration of acid is ≥0.5 to ≤20 times the concentration of Ruthenium (in mol:mol). It has been found that by doing so the reaction speed and the TON can be increased for many applications within the present invention. More preferred the concentration of acid is ≥0.8 to ≤10 times the concentration of Ruthenium (in mol:mol), yet more preferred ≥1 to ≤2 times.

According to a preferred embodiment of the present invention, step a) is performed under acidic conditions whereby the acid is selected out of the group comprising organic or inorganic acids, especially sulfonic acids, especially methanesulfonic acid, trifluormethansulfonic acid, p-toluolsulfonic acid, p-bromobenzosulfonic acid, p-nitrobenzosulfonic acid, sulfuric acid, hydrochloric acid, hydrofluoric acid, trifluoracetic acid, perchloric acid or mixtures thereof. Even more preferred are acids which provide weak coordinating anions after deprotonation, such as bis(trifluoromethane)sulfonimide or mixtures thereof with aforementioned acids. These compounds have proven themselves in practice.

According to a preferred embodiment of the present invention, step a) is carried out at a temperature of ≥0° C. to ≤250° C., preferably ≥20° C. to ≤230° C., more preferred ≥60° C. to ≤210° C., even more preferred ≥120° C. to ≤200° C. and most preferred at ≥150° C. to ≤180° C. This has been shown to be most efficient for most applications within the present invention.

According to a preferred embodiment of the present invention, step a) is carried out in a dipolar protic or aprotic solvent or in $CO_2$. Preferred solvents are ethers, also cyclic ethers such as THF or 1,4-dioxane and $CO_2$ (either liquid or near or supercritical). $CO_2$ is for some applications of the present invention insofar a preferred solvent since it is also one of the possible educts.

Of couse if the organic molecule to be reduced is liquid (and preferably the reaction product, too) then according to an alternative preferred embodiment of the present invention, step a) can be carried out without any solvent.

According to a preferred embodiment of the present invention, step a) is carried out at an initial hydrogen pressure of ≥1 bar, preferably ≥10 bar and most preferred ≥20 bar. This has been shown to greatly increase the reaction speed and efficiency for most applications of the present invention.

In case $CO_2$ is a reactand, it is especially preferred that step a) is carried out at an initial $CO_2$ pressure of ≥1 bar, preferably ≥5 bar and most preferred ≥10 bar. This has been shown to greatly increase the reaction speed and efficiency for most applications of the present invention, too.

According to a preferred embodiment of the present invention, the method furthermore comprises a step a0) to be performed before step a):

a0) Reacting suitable precursor compounds to form the Ruthenium-Triphosphine-complex The precursor can be a salt or complex containing ruthenium, independent of its formal oxidation state. Suitable Ruthenium-containing precursor compounds include Ru(acac)$_3$, [Ru(cod)(methylallyl)$_2$] Ru(nbd)(methylallyl)$_2$, Ru(ethylene)$_2$(methylallyl)$_2$, [(cod)RuCl$_2$]$_n$, RuCl$_3$, [(PPh$_3$)$_3$ Ru(H)(CO)Cl] or [(cymanthren)RuCl$_2$]$_2$.

Step a0) may be carried out at room temperature or at the same temperature at step a).

The aforementioned components, as well as the claimed components and the components to be used in accordance with the invention in the described embodiments, are not subject to any special exceptions with respect to their size, shape, material selection and technical concept such that the selection criteria known in the pertinent field can be applied without limitations.

Additional details, characteristics and advantages of the object of the invention are disclosed in the subclaims and the following description of the respective Examples which are for illustration of the invention only and non-binding.

EXAMPLES

In the following, the following catalyst systems are used, being referred to as 1b, 2b (both comparative) and 3b (inventive):

These are made according to the following synthesis scheme:

a) Synthesis of the Triphosphine Compound

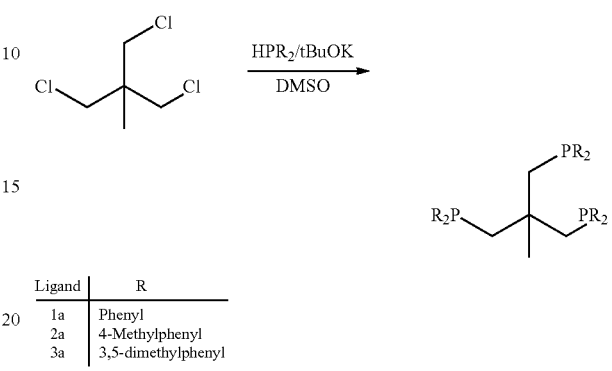

| Ligand | R |
|---|---|
| 1a | Phenyl |
| 2a | 4-Methylphenyl |
| 3a | 3,5-dimethylphenyl | b) Synthesis of the Ruthenium-Complex

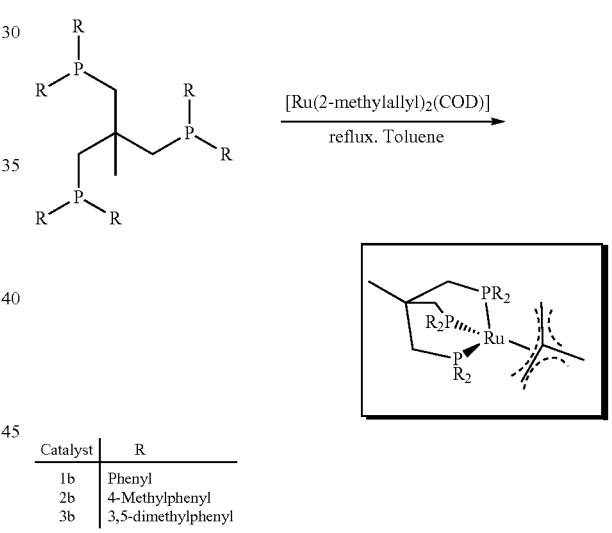

| Catalyst | R |
|---|---|
| 1b | Phenyl |
| 2b | 4-Methylphenyl |
| 3b | 3,5-dimethylphenyl |

These complexes were then used for the hydrogenation of Dimethyl itaconate. This model compound was selected since it comprises an alkene and two ester moieties. Full hydrogenated reaction products are either 2-Methyl-1-4-Butanediol (BDO) or the cyclic form 3-Methyotetrahydrofuran (3-MTHF).

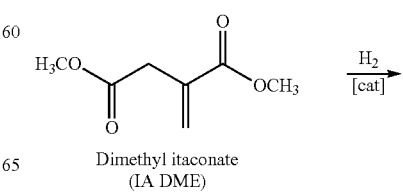

Dimethyl itaconate
(IA DME)

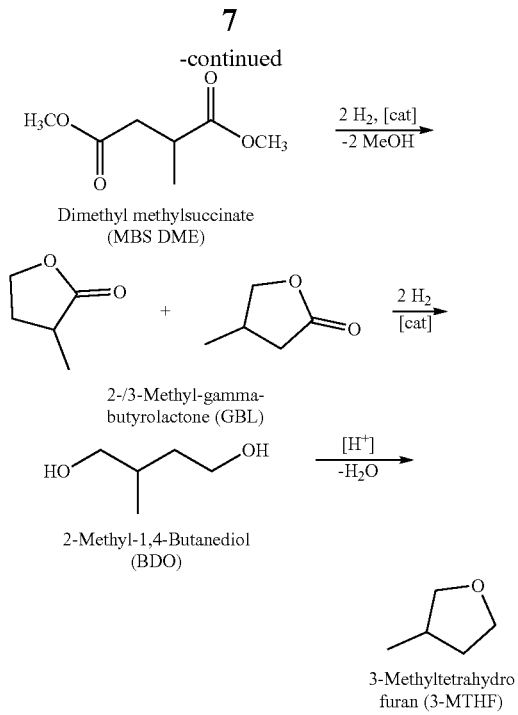

In case the hydrogenation is not complete, also Dimethyl methylsuccinate (MBS DME) and/or 2/3-Methyl-γ-Butyrolactone (MGBL) may be found as reaction products.

General Procedure for Hydrogenation Experiments

For the hydrogenation experiments the following general procedure, here exemplified with Ruthenium(Triphos-Xyl)TMM (1b) was used except where noted A 20 mL stainless steel autoclave with a glass inlet was charged with Dimethyl itaconate (3.7258 g, 23.6 mmol), Ruthenium(Triphos-Xyl)TMM (1b) (0.0095 g, 0.01 mmol) and HBTA=Bis(trifluormethylsulfon)imid (0.0028 g, 0.01 mmol). It should be noted that the ratio of catalyst/HBTA is always set 1:1 (mol/mol), also when different concentration of catalyst were used.

The autoclave was sealed, evacuated at high vacuum and refilled with argon at least 3 times and subsequently pressurized with 100 bar $H_2$ and placed into a steel cone preheated to 200° C. on a magnetic stir plate. Stirring speed was increased from 0 rpm to 700 rpm within 5 minutes to assure the movement of the stirring bar. Due to the high substrate loading the autoclave needed to be repressurized several times with $H_2$ to 100 bar. After no pressure drop was observable, the autoclave was cooled to 0° C. in an ice bath and was than depressurized to ambient pressure.

Using the general procedure, a series of test hydrogenations were made. The results are listed in the following table (average results out of three test reactions):

| Entry | Catalyst | S/C | MBSDME (in %) | MGBL (in %) | BDO (in %) | 3-MTHF (in %) |
|---|---|---|---|---|---|---|
| 1 | 1b | 1000 | 0 | 2 | 2 | 88 |
| 2 | 1b | 2000 | 23 | 10 | 0 | 35 |
| 3 | 2b | 1000 | 2 | 2 | 1 | 93 |
| 4 | 2b | 2000 | 3 | 1 | 7 | 81 |
| 5 | 3b | 1000 | 2 | 2 | 1 | 94 |
| 6 | 3b | 2360 | 0 | 0 | 77 | 20 |
| 7 | 3b | 2000 | 0 | 5 | 1 | 87 |

However in the reaction corresponding to entry 7 additionally 0.2 ml $H_2O$ were given to the reaction. "S/C" means the ratio of substrate/catalyst (in mol/mol). The further abbreviations are explained above.

It can be seen from the table that when a concentration of substrate/catalyst S/C of 2000 more is used, as in entries 2, 4 and 6 the inventive catalyst is clearly superior over the catalyst 1b and also 2b. This is quite surprising when taking into account that comparative catalyst 2b has a substitution in para-position, which is a strong indication that the ortho and/or meta-substitution has a great effect. 2b, however is not as efficient as the unsubstituted catalyst 1b.

Furthermore it could be found that even at a much lower concentration (2360 vs. 1000) the inventive catalyst is still active and even has higher TONs as with the higher concentration, whereas with the comparative catalyst 1b it is the contrary, here significant non-reduced products are found. Catalyst 2b behaves similar as 1b, although here the differences are not as strong.

Even when adding significant amounts of water—which would usually be expected to lead to a complete inertness of the catalyst—the inventive catalyst was still active and gave only minor amounts of not fully reduced byproducts, but not of MBSDME as it was the case with the other catalysts in the absence of water.

The particular combinations of elements and features in the above detailed embodiments are exemplary only; the interchanging and substitution of these teachings with other teachings in this and the patents/applications incorporated by reference are also expressly contemplated. As those skilled in the art will recognize, variations, modifications, and other implementations of what is described herein can occur to those of ordinary skill in the art without departing from the spirit and the scope of the invention as claimed. Accordingly, the foregoing description is by way of example only and is not intended as limiting. In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage. The invention's scope is defined in the following claims and the equivalents thereto. Furthermore, reference signs used in the description and claims do not limit the scope of the invention as claimed.

The invention claimed is:

1. A method for the reduction of organic molecules, comprising the step of
   a) hydrogenating at least one organic molecule in the presence of a Ruthenium-Triphosphine-complex whereby the triphosphine-complex comprises at least one aryl and/or heteroaryl moiety bound to a phosphine which is substituted in ortho and/or meta position to the phosphine such that the ruthenium center of the Ruthenium-Triphosphine-complex is shielded to prevent inactivation due to formation of a ruthenium dimer, wherein the organic molecules are selected from the group consisting of carboxylic acids, derivatives of carboxylic acids selected from the group consisting of esters, lactones and amides and derivatives of carbonic acids selected from the group consisting of CO2, carbamates, urethanes and ureas.

2. The method according to claim 1, wherein the Ruthenium-Triphosphine-complex comprises a phosphororganic compound where two or all three phosphors have an aryl and/or heteroaryl moiety which is substituted in ortho and/or meta position to the phosphine bound thereto.

3. The method according to claim 1, wherein the Ruthenium-Triphosphine-complex comprises a phosphororganic compound of the following structure

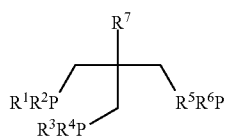

whereby $R^1$ to $R^6$ are independent from each other substituted or unsubstituted aryl or heteroaryl, provided that one of $R^1$ and $R^2$, $R^3$ and $R^4$, $R^5$ and $R^6$ is substituted in ortho and/or meta position to the phosphine, and $R^7$ is hydrogen or an organic moiety selected from the group consisting of an alkyl moiety, a cycloalkyl moiety and an aryl moiety.

4. The method according to claim 1, wherein step a) is performed under acidic conditions.

5. The method according to claim 1, wherein step a) is performed under acidic conditions whereby the initial concentration of acid is ≥0.5 to ≤20 times the concentration of Ruthenium in mol:mol.

6. The method according to claim 5, wherein step a) is performed under acidic conditions whereby the acid is a sulfonic acid.

7. The method according to claim 1, wherein step a) is carried out at an initial hydrogen pressure of ≥1 bar.

8. The method according to claim 1, wherein step a) is carried out in a dipolar protic or aprotic solvent or in $CO_2$.

9. The method according to claim 6, wherein the sulfonic acid is selected from the group consisting of methanesulfonic acid, trifluoromethanesulfonic acid, p-toluenesulfonic acid, p-bromobenzosulfonic acid, p-nitrobenzosulfonic acid, sulfuric acid, hydrochloric acid, hydrofluoric acid, trifluoroacetic acid, perchloric acid, bis(trifluoromethane)sulfonimide and mixtures thereof.

10. The method according to claim 1, wherein the carboxylic acid derivatives are selected from the group consisting of esters, lactones and amides and wherein the carbonic acid derivatives are selected from the group consisting of $CO_2$, carbamates, urethanes and ureas.

11. The method according to claim 10, wherein the Ruthenium-Triphosphine-complex comprises a phosphororganic compound where two or all three phosphors have an aryl and/or heteroaryl moeity which is substituted in ortho and/or meta position to the phosphine bound thereto.

12. The method according to claim 10, wherein the Ruthenium-Triphosphine-complex comprises a phosphororganic compound of the following structure

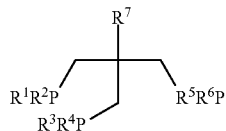

whereby $R^1$ to $R^6$ are independent from each other substituted or unsubstituted aryl or heteroaryl, provided that one of $R^1$ and $R^2$, $R^3$ and $R^4$, $R^5$ and $R^6$ is substituted in ortho and/or meta position to the phosphine, and $R^7$ is hydrogen or an organic moiety selected from the group consisting of an alkyl moiety, a cycloalkyl moiety and an aryl moiety.

13. The method according to claim 10, wherein step a) is performed under acidic conditions.

14. The method according to claim 10, wherein step a) is performed under acidic conditions whereby the initial concentration of acid is ≥0.5 to ≤20 times the concentration of Ruthenium in mol:mol.

15. The method according to claim 14, wherein step a) is performed under acidic conditions whereby the acid is a sulfonic acid.

16. The method according to claim 10, wherein step a) is carried out at an initial hydrogen pressure of ≥1 bar.

17. The method according to claim 10, wherein step a) is carried out in a dipolar protic or aprotic solvent or in $CO_2$.

18. The method according to claim 15, wherein the sulfonic acid is selected from the group consisting of methanesulfonic acid, trifluoromethanesulfonic acid, p-toluenesulfonic acid, p-bromobenzosulfonic acid, p-nitrobenzosulfonic acid, sulfuric acid, hydrochloric acid, hydrofluoric acid, trifluoroacetic acid, perchloric acid, bis(trifluoromethane)sulfonimide and mixtures thereof.

* * * * *